United States Patent [19]

Adema et al.

[11] Patent Number: 5,552,296
[45] Date of Patent: Sep. 3, 1996

[54] METHOD FOR THE DETERMINATION OF COAGULATION PARAMETERS

[75] Inventors: Enno Adema, Tutzing; Ulrike Gebert, Seeshaupt; Reinhard Herz, Poecking/Possenhofen, all of Germany

[73] Assignee: Boehringer Mannheim GmbH, Mannheim, Germany

[21] Appl. No.: 380,184

[22] Filed: Jan. 30, 1995

[30] Foreign Application Priority Data

Jan. 29, 1994 [DE] Germany .......................... 44 02 631.5

[51] Int. Cl.$^6$ .............................. C12Q 1/56; C12Q 1/00; G01N 33/53; G01N 31/00
[52] U.S. Cl. ................ 435/13; 435/4; 435/7.25; 435/69.6; 435/975; 435/810; 436/16; 436/18; 436/63; 436/74; 514/822; 514/834
[58] Field of Search ................ 435/13, 4, 7.25, 435/69.6, 975, 810; 436/16, 18, 63, 74; 514/822, 834

[56] References Cited

U.S. PATENT DOCUMENTS 4,968,494 11/1990 Claremon et al. .................... 435/13
5,185,149 2/1993 Bladwin et al. ...................... 435/13

OTHER PUBLICATIONS

Nelson et al, Blood, vol. 52/3, pp. 581–591, (Abstract) 1978.

*Primary Examiner*—John Kight
*Assistant Examiner*—Louise N. Leary
*Attorney, Agent, or Firm*—Nikaido, Marmelstein, Murray & Oram LLP

[57] ABSTRACT

In a method for the determination of coagulation parameters in sample material via a reaction cascade in which a thrombin-catalyzed formation of a fibrin clot from fibrin monomers occurs and the formation of the fibrin clot is measured, an inhibitor of F XIII is added. By this means the reaction vessel can be used several times for coagulation tests.

18 Claims, No Drawings

METHOD FOR THE DETERMINATION OF COAGULATION PARAMETERS

The invention concerns a method for the determination of coagulation parameters in which inhibitors of the activation of F XIII, F XIII$_A$ or the fibrin cross-linking activity of F XIII$_A$ are added.

The determination of coagulation parameters in sample material usually involves a reaction cascade (cf. Haemostasis 20 (suppl. 1) 14–29, 1990). In a multitude of determinations the last step is the formation of a fibrin clot catalyzed by thrombin. In this manner it is for example possible to determine PT (prothrombin time), PTTa (partial thromboplastin time activated), fibrinogen, factors II, V, VII, VIII, IX, X, XI, XII, protein C, protein S and APC resistance (see for example Bergmeyer (editor) (1988): Methods of Enzymology, Vol. V, 3rd edition; Guglumone and Vides (1992): Thromb Haemostas 67, 46-9; Preda et al (1990): Thromb Res. 60, 19–32 or Dahlbäck et al (1993): Proc Natl. Acad. Sci. USA 90, 1004-8). These references are herein incorporated by reference into the present application. Since the fibrin clot which forms cannot in practice be removed from the measuring vessels without a considerable amount of manual work, the measuring vessels are usually used only once in the determination of coagulation parameters and are subsequently discarded. Apart from the costs which this causes, such tests cannot be applied to instruments on which cuvettes are used several times. Special coagulation analysers equipped with disposable cuvettes are relatively expensive since they are only manufactured in low numbers.

The invention eliminates these disadvantages.

The invention comprises a method for the determination of coagulation parameters in sample material via a reaction cascade during which a thrombin-catalyzed formation of a fibrin clot occurs and the formation of the fibrin clot is measured which is characterized in that the determination is carried out in the presence of an inhibitor of the activation of F XIII, F XIII$_A$ or of the fibrin cross-linking activity of F XIII$_A$.

If the determination of a coagulation parameter is carried out in the presence of such an inhibitor it is subsequently possible to dissolve the fibrin clot under conditions which abolish the mutual affinity of the fibrin molecules and to remove it from the measuring vessel by rinsing processes without having an adverse effect on further determinations of coagulation parameters.

Any inhibitor of the activation of F XIII, F XIII$_A$ itself or of the fibrin cross-linking activity of F XIII$_A$ is potentially suitable.

These are for example: hydroxylamine, benzothiophene, iodoacetic acid, N-ethylmaleinimide, lanthanide ions, cefuroxime, L-arginine, L-lysine, peptide fragments of F XIII$_A$ or fibrin as well as antibodies. Examples of these inhibitors are described in the following state of the art:

Feddersen J., Gormsen J. (1976): Thromb. Haemostasis 36.
Achyuthan, E. A., Enghild, J. J., Greenberg C. S., (1991): Thromb. Haem. 65, 901.
Achyuthan, E. A., Mary and C. S. Greenberg (1989): Biochem. J. 257:331-8.
Glover C. J., L. V. McIntire, C. H. Brown and E. A. Natelson (1975): J. Lab. Clin. Med. 86:644-56.
Jiang, S. T. and J. J. Lee (1992): J. Agr. Food. Chem. 40: 1101-7.
Lee, K. N., L. Fesus S. T., Yanbcey, J. E. Girard and S. I. Chung (1985): J. Biol. Chem. 260: 14 689-94.
Samara M., J. Soria, C. Soria, M. Maamer and A. M. Otero (1979): Prog. Chem. Fibrinnolysis Thrombolysis 4: 235-40.
Lukacova, D., Matsueda, G. R., Haber, E. and Reed, G. L. (1991): Biochemistry 30: 10164-70.
Coysne C. P., Smith, J. E. and De Bowers R. M. (1992): Am. J. Vet. Res 53:695-705.
Achyuthan, K. E., Slaughter, T. F., Santiago M. A., Enghild, J. J. and Greenberg, C. S. (1993): J. Biol. Chem. 268: 21284-92.

Any solution is suitable for dissolving the clot which abolishes the mutual affinity of the fibrin molecules.

These are for example acids or bases, solutions of chaotropic ions such as KSCN or Na salicylate, urea or arginine.

The inhibitors are added at such a concentration which allows the clot to be dissolved by addition of the cleaning solution such as e.g. 1 M hydrochloric acid within a maximum of 5–10 minutes to such an extent that it can be completely removed from the measuring vessel. In the case of hydroxylamine, iodoacetic acids, N-ethyl-maleinimide this preferred concentration range is between 0.5 and 20 mmol/l.

In order to remove the fibrin clot from the measuring vessel it is preferably incubated with an acidic solution (pH<2, preferably ≦1) for a period of between 10 seconds and 10 minutes. Hydrochloric acid is preferably used for this. Subsequently it is rinsed once to three times with water or aqueous buffer solution. Afterwards the fibrin clot is removed to such an extent that further determinations of coagulation parameters are not impeded.

As an alternative to an acidic solution, it is also possible to use one of the aforementioned substances alone or in combination.

EXAMPLE 1

Procedure for a PT determination on a Hitachi 717

Sample

20 µl citrate plasma (contains ca. 5.5 g/l fibrinogen)

Reagent 1 (R1):

300 µl, 100 mmol/l Tris buffer, pH 7.0

10 mmol/l potassium chloride 2.5 mmol/l hydroxylamine and 3.75 mg/ml rabbit brain thromboplastin.

Reagent 2 (R2):

300 µl, 1 mol/l HCl

The PT determination is carried out by mixing 20 µl plasma and 300 µl R1 and measuring the time until the clot forms.

After the clot has formed, 300 µl R2 is added, mixed at 37° C. and aspirated after a further 100 seconds - for 10 minutes. It is washed once to three times with water.

An absorbance check in the measuring vessel after carrying out the determination and cleaning the measuring vessel with hydrochloric acid/water showed that the absorbance of the blank before and after the determination was not particularly different (max. ca. 0.1 mA from 50 measurements).

EXAMPLE 2

In order to examine which substances are suitable as an inhibitor of factor XIII$_A$ activity, a PT determination is carried out on a coagulometer from the H. Amelung Company, Lemgo, Germany (type KC 4A) (100 µl plasma +200 µl Neoplastin® Plus-reagent). Two minutes after the clotting has taken place, 200 µl 1 mol/l hydrochloric acid is added and the time until the ball can move freely again is measured. The results are shown in Table 1.

TABLE 1

| Substance | Concentration (mM) | Clotting time (PT 100%, s) | Ball moves after ? min |
|---|---|---|---|
| Hydroxylamine | 0.8 | 11.6 | 3.75 |
| | 1.7 | 12.2 | 1.75 |
| | 2.5 | 12.7 | 1.5 |
| | 3.3 | 13.4 | 1.5 |
| Iodoacetic acid | 0.8 | 11.7 | 2.25 |
| | 1.7 | 12.4 | 2.25 |
| | 2.5 | 13.3 | 1.75 |
| | 3.3 | 14.2 | 1.5 |
| N-ethylmaleinimide | 2.5 | 12.2 | >5 |
| | 3.3 | 12.5 | 2.25 |
| | 6.6 | 12.7 | 1.5 |
| | 10 | 13.2 | 1.75 |
| | 13.3 | 13.3 | 2 |

EXAMPLE 3

In order to examine which solutions are suitable for dissolving the clot after the measurement, a PT determination is carried out on a coagulometer from F.H. Amelung, Lemgo, Germany, type (KC 4A) (100 µl plasma + 200 µl Neoplastin®–Plus+hydroxylamine, final concentration 2.5 mM). Two minutes after the clotting has taken place, 200 µl dissolution agent is added and the time until the ball can move freely again is measured. The results are shown in Table 2.

TABLE 2

| Dissolution agent | Ball moves after ? seconds |
|---|---|
| 1 M HCl | 75 |
| 100 mM citrate, | |
| pH = 2 | >300 |
| pH = 3 | >300 |
| pH = 4 | >300 |
| pH = 5 | >300 |
| 100 mM glycine | |
| pH = 10 | >300 |
| pH = 11 | >300 |
| pH = 12 | >300 |
| pH = 13 | >300 |
| 1M NaOH | 60 |
| 2M Na salicylate + 50 mM EDTA | |
| pH = 10 | >300 |
| pH = 11 | >300 |
| pH = 12 | >300 |
| pH = 13 | 100 |

EXAMPLE 4

Procedure for a PTTa determination

The transferability of the data obtained for the PT determination was validated on a KC-4A as follows:

10 µl 100 mM hydroxylamine
100 µl plasma
100 µl PTTa reagent (Boehringer Mannheim GmbH)
3 minutes incubation
100 µl CaCl2
Measurement of the clotting time
2 minutes additional incubation
200 µl 1 M HCl
Measurement of the time until the ball moves again freely.

The results are shown in Table 3.

TABLE 3

| | Clotting time (seconds) | Ball moves after ? seconds |
|---|---|---|
| without hydroxylamine | 33.5 | >300 |
| with hydroxylamine | 34.5 | 30 |

EXAMPLE 5

Procedure for a protein C determination

The transferability of the data obtained for the PT determination was validated on a KC-4A as follows:

10 µl 100 mM hydroxylamine
10 µl plasma
90 µl Owrens buffer (Boehringer Mannheim)
100 µl R1 protein C reagent (Boehringer Mannheim)
100 µl R2 protein C reagent (Boehringer Mannheim)
3 minutes incubation
100 µl CaCl2 solution
Measurement of the clotting time
2 minutes additional incubation
200 µl 1 M HCl
Measurement of the time until the ball moves freely again.
The results are shown in Table 4.

TABLE 4

| | Clotting time (seconds) | Ball moves after ? seconds |
|---|---|---|
| without hydroxylamine | 127 | >300 |
| with hydroxylamine | 133 | 120 |

EXAMPLE 6

Procedure for a thrombin time determination

The transferability of the data obtained for the PT determination was validated on a KC-4A as follows:

20 µl 100 mM hydroxylamine
200 µl plasma
2 minute incubation
200 µl thrombin reagent (Boehringer Mannheim Order No. 126 594)
Measurement of the clotting time
2 minutes additional incubation
300 µl 1 M HCl
Measurement of the time until the ball moves freely again.
The results are shown in Table 5.

TABLE 5

| | Clotting time (seconds) | Ball moves after ? seconds |
|---|---|---|
| without hydroxylamine | 17.3 | >300 |
| with hydroxylamine | 17.1 | 80 |

We claim:

1. A method for the determination of coagulation parameters in a sample, comprising the steps of:
   forming a thrombin-catalyzed fibrin clot, and
   measuring formation of the fibrin clot, wherein the determination is carried out in the presence of an activation inhibitor of F XIII, F XIII$_A$ or the fibrin cross-linking activity of F XIII$_A$.

2. The method according to claim 1, wherein said activation inhibitor is selected from the group consisting of hydroxylamine, benzothiophene, iodoacetic acid, N-ethyl-maleinimide, lanthanide ions, cefuroxime, L-arginine, L-lysine, peptide fragments of F XIII$_A$ or fibrin, and antibodies.

3. The method according to claim 2, wherein said activation inhibitor is selected from the group consisting of hydroxylamine, iodoacetic acid and N-ethyl-maleinimide.

4. The method according to claim 3, wherein the activation inhibitor is present in a concentration between 0.5 and 20 mmol/l.

5. A method for the determination of coagulation parameters in at least two different samples, comprising the steps of:

a) forming a thrombin-catalyzed fibrin clot in a measuring vessel, b) measuring the formation of the fibrin clot, c) adding to said measuring vessel a solution which abolishes the mutual affinity of fibrin molecules, d) emptying the measuring vessel, e) washing the measuring vessel at least once, and f) repeating steps a) and b) using a different sample, wherein steps a) and b) are carried out in the presence of an activation inhibitor of F XIII, F XIII$_A$ or the fibrin cross-linking activity of F XIII$_A$.

6. The method according to claim 5, wherein said measuring vessel is washed with distilled water.

7. The method according to claim 5, wherein said solution which abolishes the mutual affinity of the fibrin molecules is selected from the group consisting of an acid, a base, solutions of chaotropic ions, urea, arginine, and combinations thereof.

8. The method according to claim 7, wherein said solution which abolishes the mutual affinity of the fibrin molecules is selected from the group consisting of an acid, a base, Na salicylate/EDTA and combinations thereof.

9. The method according to claim 5, wherein said solution which abolishes the mutual affinity of the fibrin molecules is present at a concentration which allows the clot to be dissolved in less than 5–10 minutes.

10. The method according to claim 5, wherein said solution which abolishes the mutual affinity of the fibrin molecules is 1M hydrochloric acid.

11. The method according to claim 5, wherein said activation inhibitor is selected from the group consisting of hydroxylamine, iodoacetic acids, and N-ethyl-maleinimide.

12. The method according to claim 11, wherein said activation inhibitor is present in a concentration between 0.5–20 mmol/l.

13. The method according to claim 5, wherein the pH of the sample after the addition of the solution which abolishes the mutual affinity of the fibrin molecules, is below 2 or above 13.

14. The method according to claim 5, wherein said determination is carried out using a coagulometer or a photometric analyzer.

15. A kit for the determination of coagulation parameters, comprising a) an activation inhibitor of F XIII, F XIII$_A$ or the fibrin cross-linking activity of F XIII$_A$, and b) a solution which abolishes the mutual affinity of fibrin molecules.

16. The kit according to claim 15, wherein said solution which abolishes the mutual affinity of the fibrin molecules is selected from the group consisting of an acid, a base, solutions of chaotropic ions, urea, arginine, and combinations thereof.

17. The kit according to claim 15, wherein said activation inhibitor is selected from the group consisting of hydroxylamine, iodoacetic acid and N-ethyl-maleinimide.

18. A composition produced during the determination of coagulation parameters of a sample, comprising a) a thrombin catalyzed fibrin clot formed from the sample in the presence of an activation inhibitor of F XIII, F XIII$_A$ or the fibrin cross-linking activity portion of F XIII$_A$, b) an activation inhibitor of F XIII, F XIII$_A$ or the fibrin cross-linking activity portion of F XIII$_A$, and c) a solution which abolishes the mutual affinity of any fibrin molecules.

* * * * *